United States Patent
Fau et al.

(10) Patent No.: US 6,395,053 B1
(45) Date of Patent: May 28, 2002

(54) METHOD OF FORMING METAL COLLOIDS, METAL COLLOIDS AND METHOD OF FORMING A METAL OXIDE SENSITIVE LAYER FOR A CHEMICAL SENSOR DEVICE

(75) Inventors: Pierre Fau, La Tour du Crieu; Celine Nayral, Toulouse; Bruno Chaudret, Vigoulet Auzil; Andre Maisonnat, Roquettes, all of (FR)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/322,496

(22) Filed: May 28, 1999

(51) Int. Cl.[7] .............................. B22F 9/16; B05D 7/00
(52) U.S. Cl. ...................... 75/362; 427/216; 427/217; 427/226
(58) Field of Search .............................. 427/126.3, 216, 427/217, 226; 75/362

(56) References Cited

U.S. PATENT DOCUMENTS 4,900,587 A * 2/1990 Ritsko et al. ............... 427/216
5,332,646 A * 7/1994 Wright et al. ............... 430/137

FOREIGN PATENT DOCUMENTS

| EP | 0751389 | 2/1997 | .......... G01N/27/12 |
| EP | 0795747 | 9/1997 | .......... G01N/27/12 |
| FR | 2678855 | 7/1991 | ............. B22F/9/26 |

\* cited by examiner

*Primary Examiner*—Brian K. Talbot
(74) *Attorney, Agent, or Firm*—Sarah J. Gibson; Robert A. Rodriguez

(57) ABSTRACT

A method of forming a metal colloid comprising a plurality of particles, each particle comprising a core of a metal, is described. The method comprises the steps of providing an organometallic precursor comprising the metal, combining the organometallic precursor and a solvent, which comprises water molecules, heating the combination of organometallic precursor and solvent so that the organometallic precursor decomposes to form a solution including the metal colloid and by-products, and removing the by-products to provide the metal colloid.

10 Claims, 4 Drawing Sheets

METHOD OF FORMING METAL COLLOIDS, METAL COLLOIDS AND METHOD OF FORMING A METAL OXIDE SENSITIVE LAYER FOR A CHEMICAL SENSOR DEVICE

FIELD OF THE INVENTION

This invention relates to a method of forming metal colloids and metal colloids. In particular, though not exclusively, the present invention relates to a method of forming a metal colloid for use in forming a metal oxide sensitive layer of a chemical sensor device.

BACKGROUND OF THE INVENTION

A metal oxide chemical sensor device, like a tin oxide chemical sensor device, comprises a metal oxide sensitive layer whose resistance varies when exposed to oxidising or reducing chemicals. The selectivity of the device to certain chemicals depends on the temperature at which the sensitive layer is maintained. Thus, by measuring the change in the resistance of the sensitive layer and the temperature of the sensitive layer, the concentration of a particular chemical can be determined. The well known theory of operation of these devices involves an adsorption/desorption phenomena at the surface of the sensitive layer, which is crystalline. This is explained in an article by N. Yamazoe in Sensors and Actuators B, 5, 1991, pages 7–19.

The sensitivity of such a sensor can be significantly improved by reducing the size of the metal oxide crystals which form the sensitive layer. It is therefore desirable to use small metal particles to form the metal oxide sensitive layer. These small particles are less than 0.1 micron in size, i.e. are nano sized particles, and are generally referred to as nano particles.

For tin oxide chemical sensors, it is known to use cathodic sputtering of a metallic target to obtain small tin particle. This sputtering process leads to the deposition of metallic tin particles, which particles are later oxidised into tin oxide by temperature treatment under air in a furnace. The tin particles each have a thickness 0.16–0.19 microns. FIG. 1 is a Scanning Electron Microscope (SEM) micrograph of tin sputtered particles (at a magnification of ×16553). Due to the columnar growth of the sensitive layer, which is inherent with cathodic sputtering, the particle size and sensitive layer thickness are strongly interdependent: that is, the thicker the sensitive layer, the larger the particle size. Thus, although the sputtering process ensures a well controlled particle size and also thickness of the tin oxide sensitive layer, due to the interdependence between the grain size and sensitive layer thickness, there is a limit below which the particle size cannot be reduced. In other words, it is possible to deposit by sputtering very small nano particles but in this case, the process is not under control and leas to too thin metal layers for chemical sensor applications. Details of the sputtering technique have been published in an article by V. Demarne and A. Grisel in 'Sensors and Actuators', B, 15–16 (1993) pages 63–67.

Other techniques to provide small metal particles or metal nano particles have also been explored.

An article by A. Henglein and M. Giersig in the J. Phys. Chem. 1994, 98, pages 6931–6935, describes preparing tin nano particles by radiolytic reduction of tin chloride ($SnCl_2$) using gamma radiation from a cobalt source ($^{60}Co$).

From an article in the Colloid and Polymer Science 1994, pages 272, 310, by G. Cardenas-Trino, M. Alvial, K. J. Klabunde, M. O. Pantoja, Z. H. Soto and from an article by E. Sondergard, R. Kofman, P. Cheyssac, A. Stella in the Applied Surface Science, 1996, pages 364, 467, it is also known that tin particles, which may or may not be stabilised by a polymer, can be prepared by evaporation condensation methods, either by Chemical Liquid Deposition (CLD) to yield particles having sizes in the range 15–50 nm codeposited with a solvent at 77 Kelvin, or by metal evaporation under ultra high vacuum and condensation leading to various sizes of particle (in the range of 1–150 nm), the size being a function of the growth mode.

All these solutions, however, require heavy and costly equipment, such as a radioactive source, ultra low temperature equipment, and thus cannot be realistically used on an industrial scale, for example, in the manufacture of semiconductor chemical sensors.

There is therefore a need for an improved method of forming metal nano particles.

BRIEF DESCRIPTION OF THE DRAWINGS

A method of forming a metal colloid, a metal colloid and a method of forming a metal oxide sensitive layer, will now be described, by way of example only, with reference to the accompanying drawings in which.

DETAILED DESCRIPTION OF THE DRAWINGS

The present invention prepares metal nano particles of controlled size and size distribution by synthesising a metal colloid. As used herein, metal colloid means a product comprising a plurality of metal particles, each metal particle being stabilised by a protective layer formed round the metal particle. The following description relates to the preparation of a tin colloid. However, the present invention is not limited to tin and can be used for any other metals, such as iron, ruthenium, cobalt, nickel, palladium, copper, silver, gold, platinum or bimetallic associations.

Briefly, the method of forming a tin colloid in accordance with a preferred embodiment of the present invention involves the decomposition of an organometallic precursor of tin in an solvent containing water, preferably under a controlled atmosphere (e.g. an inert gas such as argon) and at a moderately elevated temperature (100–160° C.).

Figure 2:
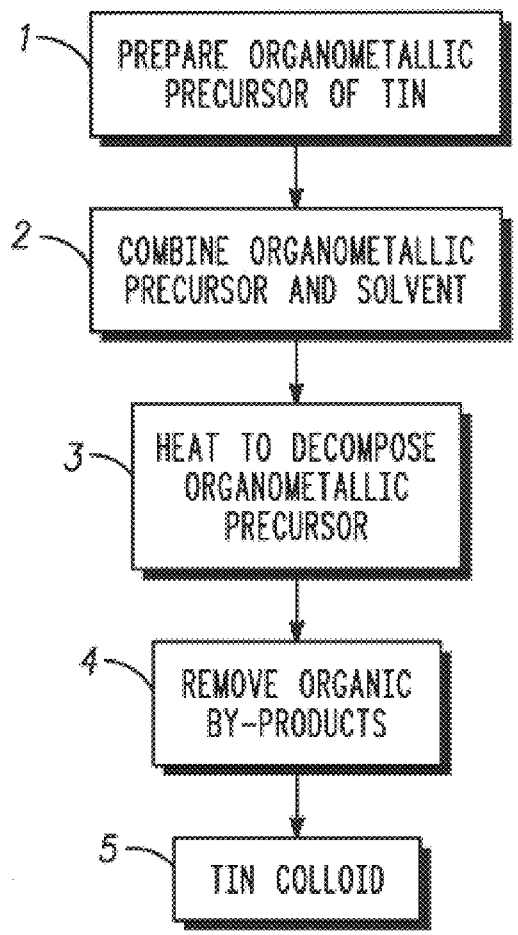
FIG. 2 is a flow chart of a method of forming a metal colloid in accordance with the present invention.

The method in accordance with the preferred embodiment of the present invention will now be described in more detail with reference to FIG. 2.

The method begins with the preparation of an organometallic precursor of tin, step 1. Synthesising an organometallic precursor of a metal is well known in the art. It is, however, preferable to select an organometallic precursor which has the lowest possible bonding energy between the metal and the organic part so as to minimise the temperature required to decompose the organometallic precursor. Of course, other precursors can be used but they would require a higher decomposition temperature. Lower decomposition temperatures are preferred to make the synthesis process simpler and also at higher temperatures it appears that it is harder to obtain small tin particles.

To keep the decomposition temperature low, in the preferred embodiment, the amido complex ($[Sn(N(CH_3)_2)_2]_2$ is selected as the organometallic precursor of tin. It is prepared by combining tin chloride with lithium dimethylamide ($LiN(CH_3)_2$) and a solvent, such as toluene, at room temperature.

The by-products of the reaction are removed by sublimation to leave an organometallic precursor of tin ($[Sn(N(CH_3)_2)_2]_2$). The first by-products (LiCl) of the reaction are precipitated at the bottom of the reaction receptacle. The supernatent (solvent and reaction products) is then transferred into another receptacle. The solvent is removed under vacuum to obtain the rough reaction product in powder form. This rough reaction product is then purified by sublimation to provide the organometallic precursor. The publication by Foley, Zeldin, in Inorganic Chemistry, vol 14, No. 9, 1975, pages 2264–2267 provides details of this procedure.

The organometallic precursor is then dissolved in a solvent, step 2. The solvent can be any solvent which comprises water molecules, e.g. a slightly hydrated solvent, such as the commercial solvent anisol or toluene. Empirically, it has been found that anisol provides the better yield.

Then, step 3, the precursor in the solvent is heated to break the bonds between the tin and the organic part of the precursor to provide a tin colloid in solution with anisol. For this particular precursor, it was found that the precursor and solvent had to be heated to a minimum temperature of 130° C. For other precursors, the minimum temperature will be determined by the minimum energy required to break the bonds between the tin and the organic part to provide a good yield (e.g. 50% in mass) of metal particles.

After decomposition of the organometallic precursor, a tin colloid plus the organic by-products are left in solution. These by-products are removed, step 4, by first removing the solution and by then washing the remaining tin colloid with pure solvent (anisol), at least three times. After this step, a pure tin colloid is provided, step 5. This very unique metal colloid can be used directly as a suspension in any solvent for, for example, spin-on applications, or else dried to a powder for other purposes.

Steps 1, 2, 3 and 4 take place under an inert gas, such as argon for stability. Since the tin colloid comprises tin particles surrounded by a protective shell, the tin colloid does not need to be kept under argon and can be kept under air.

Figure 3:
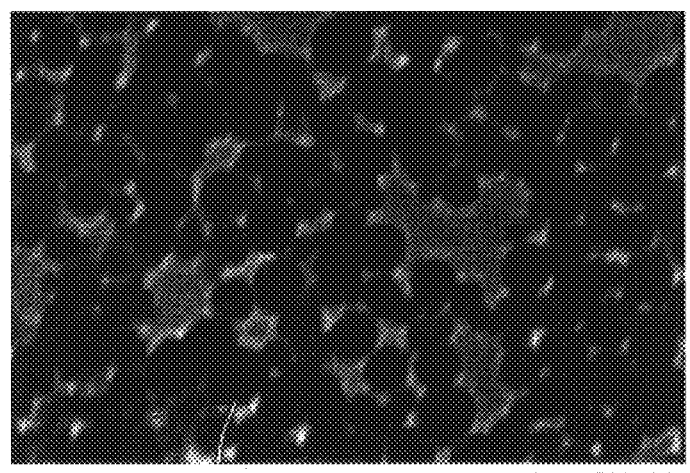
FIG. 3 is a Transmission Electron Microscope (TEM) micrograph of tin particles formed by the method in accordance with the present invention at a magnification of ×321200.
Figure 4:
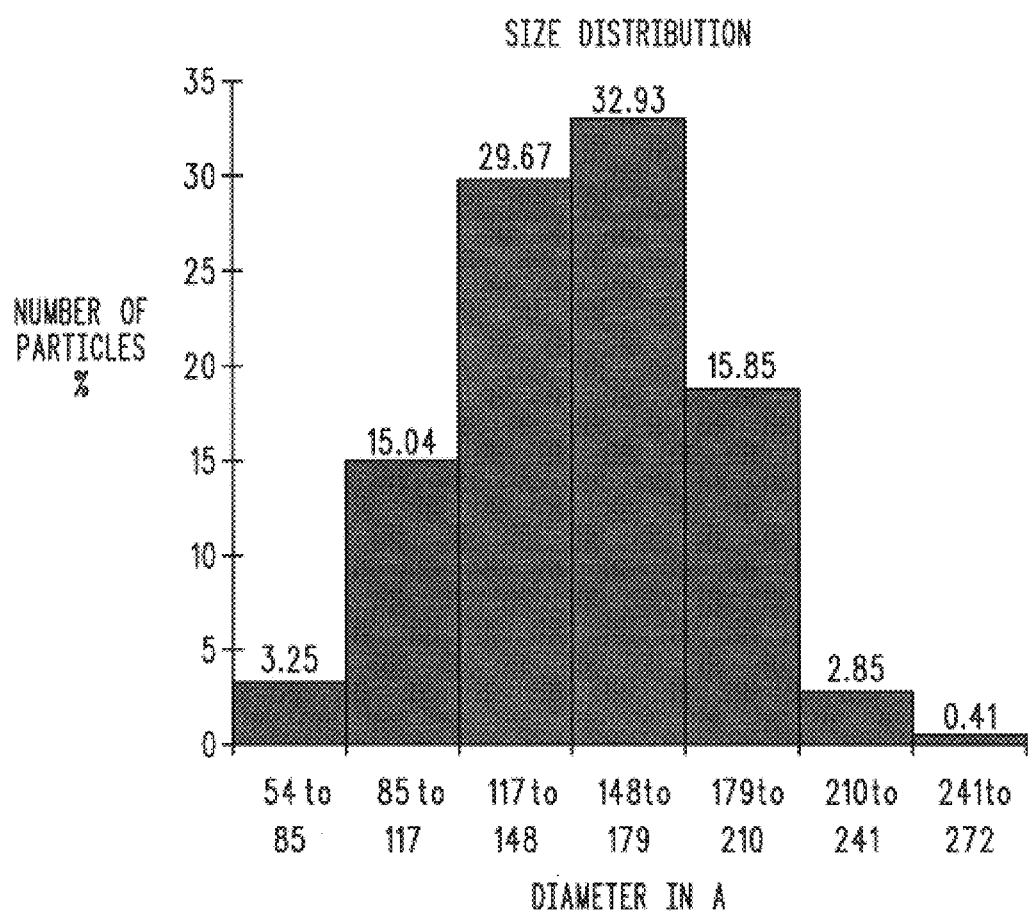
FIG. 4 is a graph showing the size distribution of the tin particles of FIG. 3.

As can be seen in FIG. 3, High Resolution Electron Microscopy (HREM) demonstrates that the tin colloid prepared by the method according to the present invention comprises tin spherical particles, which have a mean diameter of 15 nm, which display a very narrow size distribution and which are considerably dispersed. From FIG. 4, which is a graph showing the size distribution of the tin particles, it can be seen that about 90% of the particles are in the range 0.015±0.005 microns.

Figure 5:
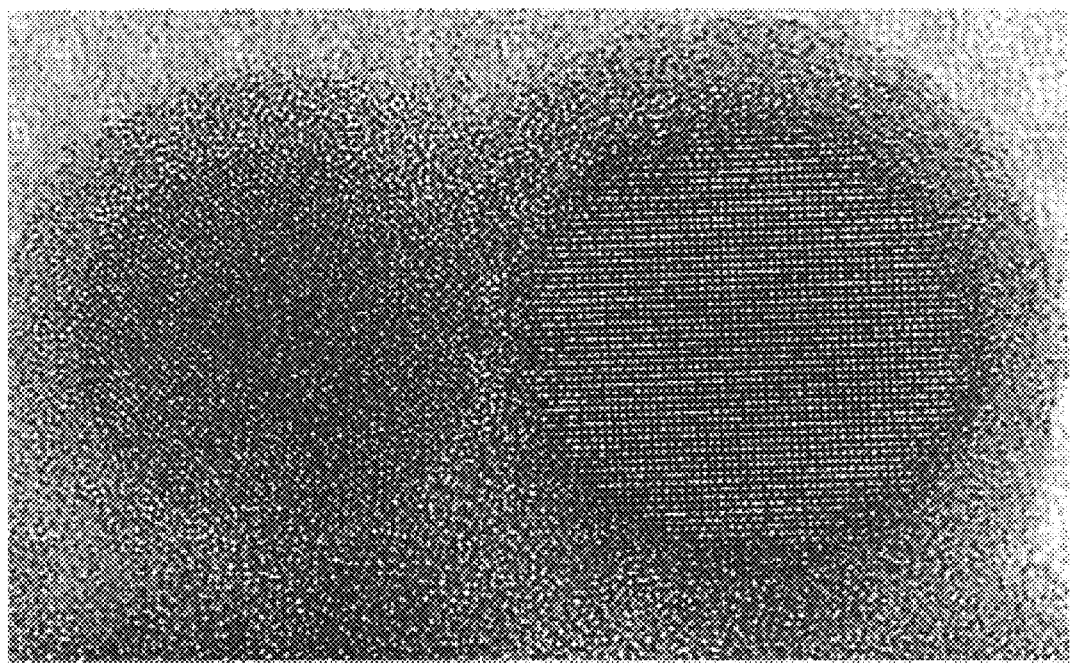
FIG. 5 is a TEM micrograph of an individual tin particle of FIG. 3 at a magnification of ×3173500.

Referring now also to FIG. 5, Energy Dispersive X-ray analysis (EDX) and X-ray Photoelectron Spectroscopy (XPS) have demonstrated that each of the tin colloid particles comprises a core constituted of pure, crystalline tin, which core is surrounded and protected by an amorphous layer of tin oxide which has a thickness of approximately 3 nm. Hence, this material is a metal and metal oxide nano composite. The amorphous tin oxide keeps each tin particle from further growing or packing.

Figure 1:
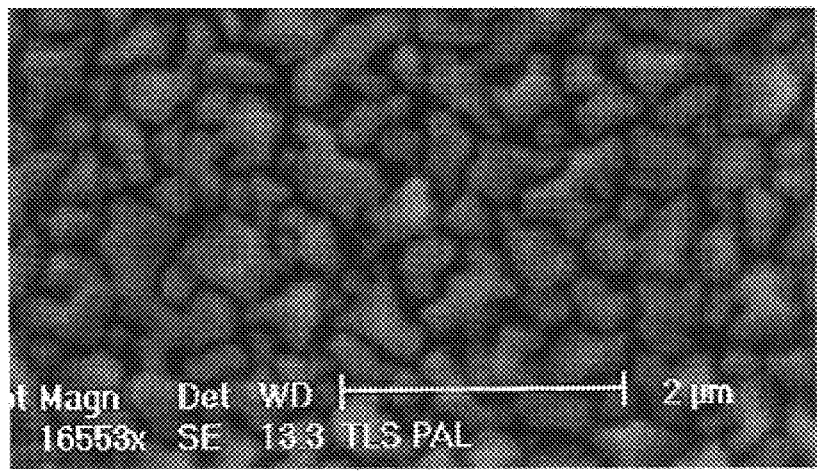
FIG. 1 is a SEM micrograph of tin sputtered particles at a magnification of ×16553.
Figure 6:
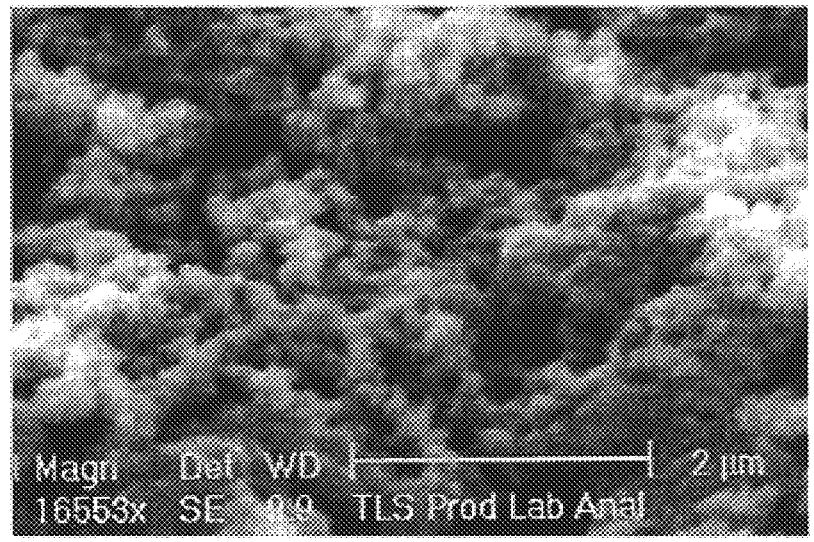
FIG. 6 is a SEM micrograph of tin particles formed by the method in accordance with the present invention at the same magnification as FIG. 1.

As mentioned above, the tin colloid formed by the method in accordance with the present invention comprises tin nano particles having a mean size of 15 nm. By comparing FIG. 1 and FIG. 6, which shows a SEM micrograph of tin particles obtained by the method in accordance with the present invention having the same magnification as FIG. 1, it can be seen that the present invention provides tin particles which are significantly smaller than those prepared by the sputtering technique. The tin colloid is therefore ideal for use in forming a tin oxide sensitive layer for a tin oxide chemical sensor device to improve the sensitivity of the sensor device. Again, tin is only an example used to illustrate the invention. Other metal colloids can be used to form the desired metal oxide sensitive layer.

Figure 7:
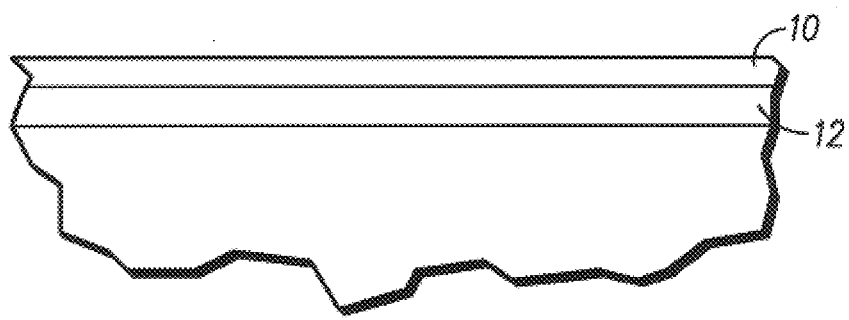
FIGS. 7–8 are simplified cross-sectional diagrams of part of a chemical sensor device during the formation of the sensitive layer.

A method of forming a tin oxide sensitive layer of a tin oxide chemical sensor using a tin colloid will now be described with further reference to FIGS. 7–9.

The tin colloid is prepared as described above. A layer 10 of the tin colloid is then formed on a dielectric layer 12, such as a silicon oxide layer, which is part of the chemical sensor device (only part of which is shown in FIG. 7). Preferably, a suspension of the tin colloid is formed in a solvent, such as anisol, and the tin colloid is then deposited on the dielectric layer 12 by, for example, a spin-on method.

The tin particles are then oxidised into tin oxide by thermal treatment under a nitrogen and oxygen blended atmosphere. Preferably, the thermal treatment comprises two main steps: a low temperature step at 200° C. which ensures slow oxidation of the tin particles to tin oxide SnO; and then a high temperature step at 650° C. in order to form the final crystalline tin oxide $SnO_2$ sensitive layer. The tin oxide nano particles, which form the sensitive layer, each have a diameter of preferably 0.02 micron. FIG. 9 is a TEM micrography of tin oxide $SnO_2$ nano particles formed from oxidation of the tin colloid. The tin oxide $SnO_2$ structure is however present after a 450° C. anneal. This type of thermal treatment is well known in this field.

Figure 8:
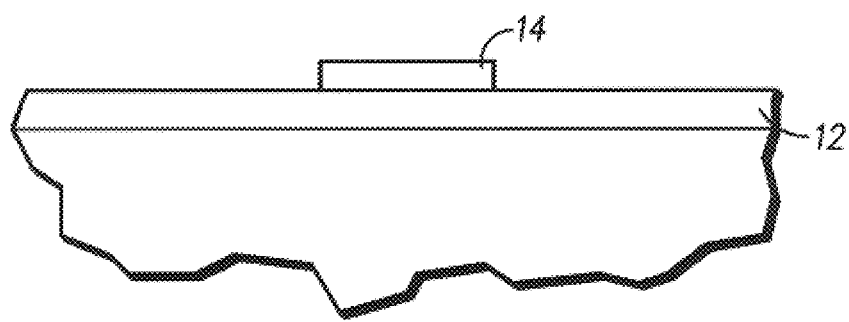
Figure 9:
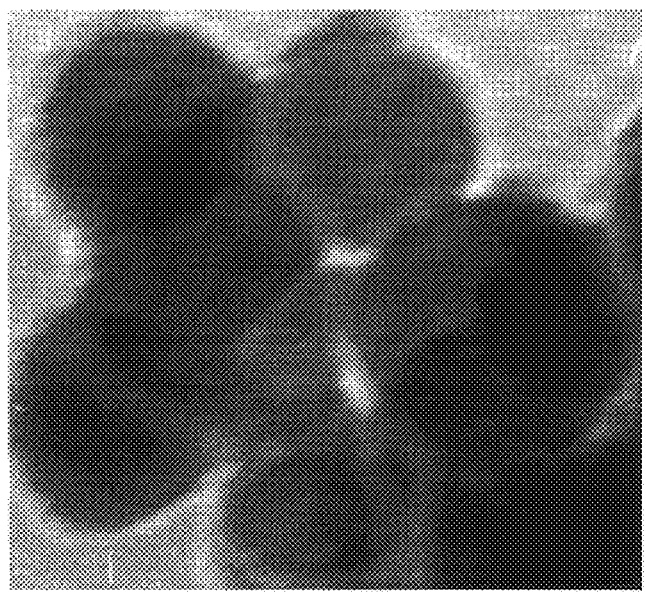
FIG. 9 is a TEM micrograph of tin oxide nano particles formed from the tin colloid in accordance with the present invention at a magnification of ×2145000.

The tin oxide layer is then patterned and etched to leave a sensitive layer 14 of tin oxide on the chemical sensor device (FIG. 8).

The metal colloid is formed on the semiconductor layer at the same point the processing of the chemical sensor device as would be the case if sputtering of a metallic target was used. Also, the subsequent processing steps are the same. Thus, the other process steps will not be described in detail. For details, reference can be made to European patent application no. EP 97101015.2 (SC0464ET) and European patent application no. EP 97401796.4 (SC0606ET).

In an article by A. Dieguez, A. Romano-Rodriguez et al. entitled 'Morphological analysis of nanocrystalline $SnO_2$ for gas sensor applications' in Sensor and Actuators B 31 (1996), pages 1–8, it has been reported that different ways of synthesis (e.g. sol-gel method, which method is based on the synthesis of the hydroxide compound of the desired metal, e.g. $Sn(OH)_4$ which is then precipitated by the action of a basic solution e.g. $NH_3$) of nanocrystalline tin oxide particles lead to a marked increase of mean particle size when oxidised at temperatures ranging from 450° C. to 800° C. The authors of this article found that the powders annealed at 450° C. have an average particle size of about 20 nm but after a 800° C. anneal, the distribution spreads to around 1000 nm and the particles undergo a faceting effect (loss of the initial spherical shape).

An advantage of using the tin colloid in accordance with the present invention for forming a tin oxide sensitive layer is that both the spherical shape and the particle size remains substantially unaffected after annealing and oxidation. This appears to be due to the fact that the starting material of tin colloid comprises spherical nano particles of tin covered by tin oxide. The tin oxide material protects the tin particle from growing and faceting.

Tests were carried out for three high temperature oxidation anneals 450° C., 650° C. and 750° C. The resulting tin oxide material was analysed by means of X-ray diffraction (structure, mean particle size) and a Transmission Electron Microscope (TEM) (particle size, shape distribution). The results showed that the tin oxide particle size did not change within the described range of temperature and remained in the region of 30 nm maximum. Moreover, there was no spreading of the size distribution. The shape remained spherical with very few faceting phenomena at the highest temperature (750° C.). Hence, with the tin colloid material in accordance with the present invention, it is possible to keep, even at high temperatures, the advantages of very small tin oxide particles.

In summary, the present invention provides a method of forming a metal colloid comprising a plurality of particles, each particle comprising a core of a metal, the method comprising the steps of:

providing an organometallic precursor comprising the metal;

combining the organometallic precursor and a solvent, the solvent comprising water molecules;

heating the combination of organometallic precursor and solvent so that the organometallic precursor decomposes to form a solution including the metal colloid and organic by-products; and removing the organic by-products to provide the metal colloid.

In other words, the present invention provides a method for forming a metal colloid which comprises metal particles of controlled nano size (<50 nm) and size distribution by the decomposition of organometallic precursors in the presence of a lightly hydrated solvent (like anisol) and with or without stabilising polymers (e.g. PPO added to anisol, PPO=Poly 2–6 dimethyl 1–4 phenylene oxide). The presence of polymers is not mandatory to form the spherical tin colloid but can help for a better dispersion of the product.

Advantages of the method in accordance with the invention compared to other methods are the following:

i) the use of organometallic precursors excludes the presence of unwanted by-products. With the method in accordance with the present invention, the simple thermal decomposition of the organometallic precursor leads to easily purified tin colloids. Generally, other methods use a complementary agent (reducing agent) to achieve the transformation of the precursor into the desired metal colloid. This reducing agent is a high potential source of pollutant. For example, it can contaminate the surface of the colloidal particle;

ii) the preparation of the metal colloid occurs in solution, generally in very mild conditions, in the presence or not of a reducing gas, such as hydrogen or carbon monoxide gas, i.e. non-polluting gases, which means that these adjustable parameters (solvent, additives, temperature, pressure) allow good control of the particles' growth and hence their size and morphology; and iii) the method of forming the metal colloid involves classical chemical procedures which means that the scale-up of the process for industrial requirements will be easy.

The advantages of the metal colloid in accordance with the present invention make it particularly desirable for use as the starting material for forming a metal oxide sensitive layer of a chemical sensor device.

What is claimed is:

1. A method of forming a metal colloid comprising a plurality of particles, each particle comprising a core of a metal, the method comprising the steps of:

providing an organometallic precursor comprising the metal;

combining the organometallic precursor and a solvent, the solvent comprising water molecules;

heating the combination of organometallic precursor and solvent so that the organometallic precursor decomposes to form a solution including the metal colloid and by-products wherein the decomposition of the organometallic precursor is performed without the aid of a reducing agent; and removing the by-products to provide the metal colloid.

2. A method of forming a metal colloid according to claim 1, wherein the heating step comprises heating the combination to a predetermined temperature, the predetermined temperature depending on the bonding energy between the metal and an organic compound which form the organometallic precursor.

3. A method of forming a metal colloid according to claim 1 wherein, the providing step, the heating step and the combining step takes place under an inert gas.

4. A method of forming a metal colloid according to claim 1, wherein the removing step comprises the steps of:

removing the solution; and washing the metal colloid in a pure solvent.

5. A method of forming a metal colloid according to claim 1 wherein the solvent is selected from the following solvents: anisol, and toluene.

6. A method of forming a metal oxide sensitive layer for a chemical sensor device comprising the steps of:

forming a metal colloid comprising a plurality of particles, each particle comprising a core of a metal, the forming a metal colloid step comprising the steps of:

providing an organometallic precursor comprising the metal, combining the organometallic precursor and a solvent, the solvent comprising water molecules, heating the combination of organometallic precursor and solvent so that the organometallic precursor decomposes to form a solution including the metal colloid and by-products wherein the decomposition of the organometallic precursor is performed without the aid of a reducing agent; and removing the by-products to provide the metal colloid;

forming a layer of the metal colloid on a semiconductor layer which layer is part of the chemical sensor device;

oxidising the metal colloid layer to provide a metal oxide layer on the semiconductor layer; and removing a portion of the metal oxide layer, a remaining portion of the metal oxide layer forming the metal oxide sensitive layer.

7. A method of forming a metal colloid according to claim 6, wherein the heating step comprises heating the combination to a predetermined temperature, the predetermined temperature depending on the bonding energy between the metal and an organic compound which form the organometallic precursor.

8. A method of forming a metal colloid according to claim 6 wherein, the providing step, the heating step and the combining step takes place under an inert gas.

9. A method of forming a metal colloid according to claim 6, wherein the removing step comprises the steps of:
   removing the solution; and
   washing the metal colloid in a pure solvent.

10. A method of forming a metal colloid according to claim 6 wherein the solvent is selected from the following solvents: anisol, and toluene.

* * * * *